(12) United States Patent
Lin et al.

(10) Patent No.: US 6,520,915 B1
(45) Date of Patent: Feb. 18, 2003

(54) ULTRASOUND IMAGING SYSTEM WITH INTRINSIC DOPPLER CAPABILITY

(75) Inventors: Shengtz Lin, Cupertino, CA (US); Hue Phung, Cupertino, CA (US)

(73) Assignee: U-Systems, Inc., Los Altos, CA (US)

( * ) Notice: Subject to any disclaimer, the term of this patent is extended or adjusted under 35 U.S.C. 154(b) by 0 days.

(21) Appl. No.: 09/721,888

(22) Filed: Nov. 24, 2000

Related U.S. Application Data

(63) Continuation-in-part of application No. 09/493,396, filed on Jan. 28, 2000, now Pat. No. 6,248,071.

(51) Int. Cl.[7] .................................................. A61B 8/00

(52) U.S. Cl. ....................... 600/453; 600/455; 600/443

(58) Field of Search ................................. 600/454, 443, 600/441, 447, 456, 449, 455, 453; 128/916

(56) References Cited

U.S. PATENT DOCUMENTS

| | | | |
|---|---|---|---|
| 5,228,009 A | | 7/1993 | Forestieri et al. |
| 5,437,281 A | | 8/1995 | Lin et al. |
| 5,445,156 A | | 8/1995 | Daft et al. |
| 5,482,044 A | | 1/1996 | Lin et al. |
| 5,904,653 A | * | 5/1999 | Hatfield et al. .............. 128/916 |
| 5,938,611 A | | 8/1999 | Muzilla et al. |
| 5,980,459 A | | 11/1999 | Chiao et al. |
| 6,045,507 A | * | 4/2000 | Muzilla et al. .............. 600/443 |
| 6,068,598 A | * | 5/2000 | Pan et al. .................... 600/453 |
| 6,074,348 A | | 6/2000 | Chiao et al. |
| 6,126,603 A | * | 10/2000 | Hatfield et al. .............. 600/443 |
| 6,350,241 B1 | * | 2/2002 | Lifshitz ........................ 600/454 |

FOREIGN PATENT DOCUMENTS

| | | |
|---|---|---|
| EP | 0948931 | 10/1999 |
| WO | WO 9956626 | 11/1999 |

OTHER PUBLICATIONS

James A. Zagzebski, *Essentials of Ultrasound Physics* (1996) (title page and table of contents).
www.intersil.com/data/fn/fn3/fn3365/fn3365.pdf.
www.intersil.com/data/an/an9/an9063/an9603/pdf.
Carlson, *Communication Systems: An introduction to Signal and Noise in Electrical Communication*, (McGraw–Hill, 3rd ed. 1986).
Couch, *Digital and Analog Communications System*, (MacMillan, 3rd ed. 1990) at pp. 497–503.

* cited by examiner

*Primary Examiner*—Francis J. Jaworski
*Assistant Examiner*—Maulin Patel
(74) *Attorney, Agent, or Firm*—Cooper & Dunham LLP

(57) ABSTRACT

An ultrasound imaging system capable of generating a flow image from B-mode echo frames. For each location in a target region, phase information is derived from the B-mode echo frames, and frame-to-frame changes in the phase information are processed to detect the presence of fluid flow at that location. A demodulator receives the B-mode echo frames and demodulates them into baseband signal components from which the phase information is derived. Preferably, the demodulator is highly accurate and robust, such that frame-to-frame changes in the phase information are reliably measured. From the reliably measured phase information, a phase shift metric is then computed and thresholded by a user-adjustable threshold value. Flow is present if the phase shift metric is greater than the threshold value and is absent otherwise. The user may adjust the threshold value in real time through an input device, such as a knob or keyboard, to increase or decrease the flow sensitivity as desired and/or to eliminate the slow-moving clutter. Together with a B-mode image, the flow image is provided to an ultrasound display. For further clutter removal, the flow image may be suppressed for those locations having B-mode intensities below a predetermined lower threshold or above a predetermined upper threshold. The provided system provides a real-time flow image having the same high frame rate, spatial resolution, and coverage area as the B-mode image.

31 Claims, 8 Drawing Sheets

ULTRASOUND IMAGING SYSTEM WITH INTRINSIC DOPPLER CAPABILITY

CROSS-REFERENCE TO RELATED APPLICATIONS

This application is a continuation-in-part of U.S. patent application Ser. No. 09/493,969, entitled "Demodulating Wide-Band Ultrasound Signals," filed Jan. 28, 2000, now U.S. Pat. No. 6,248,071, which is assigned to the assignee of the present invention, and which is incorporated by reference herein.

FIELD

This patent specification relates to the field of ultrasound information processing. In particular, it relates to a method and system for detecting and displaying fluid flow in medical ultrasound applications.

BACKGROUND

In recent decades ultrasonic imaging technology has played an increasing role in examining the internal structure of living organisms. The technology has applications in diagnosis of various medical ailments where it is useful to examine structural details in soft tissues within the body. Ultrasound imaging systems are advantageous for use in medical diagnosis as they are non-invasive, easy to use, and do not subject patients to the dangers of electromagnetic radiation. Instead of electromagnetic radiation, an ultrasound imaging system transmits sound waves of very high frequency (e.g., 2 MHz to 10 MHz) into the patient and processes echoes reflected from structures in the patient's body to derive and display information relating to these structures.

As described in Zagzebski, *Essentials of Ultrasound Physics* (Mosby 1996), which is incorporated by reference herein, principal pulse-echo ultrasound display modes includes A-mode (amplitude mode), B-mode (brightness mode), and M-mode (motion mode). An A-mode (amplitude mode) display is a simple plot of instantaneous echo amplitude versus time, measured after the transmission of an acoustic pulse along a single line of a target region. A B-mode (brightness mode) image is a two-dimensional intensity image of echo amplitude for all points in a target region, measured and continually refreshed as acoustic pulses are transmitted along different lines in the target region. An M-mode (motion mode) display is a one-dimensional intensity image of echo amplitude along a single line in the target region that is slowly swept across the screen as time moves forward. Of these principal echo display modes, only the B-mode display provides an actual 2-D "visual" representation of the acoustic reflectivity of tissues in the target region.

More recently, ultrasonic imaging systems have additionally been able to detect fluid flow (e.g., blood flow) in a target region. The detection and measurement of fluid flow is based on the Doppler effect, whereby returned acoustic signals reflected from the flowing fluid are shifted in frequency with respect to the incident interrogating signals. In color Doppler imaging, also referred to as color flow imaging, a sequence of pulses is transmitted down each line in the target region, and phase changes in the echo signals are detected and processed to determine the direction and velocity of fluid flow for each location in the target region. As known in the art, the measured flow direction is only a binary metric—either "toward" or "away from" the transducer—because fluid flow can only be detected in terms of its projection along the path of the incident interrogating pulse. Thus, the true fluid velocity can only be measured to within a factor of $\cos(\theta_d)$, where $\theta_d$ is the angle between the actual fluid flow direction and the path of the incident interrogating pulse. The term Doppler frame is used herein to denote a timewise-adjacent sequence of pulses for determining fluid velocity at each location in a target region.

In conventional color Doppler imaging, color Doppler frames are transmitted during time intervals lying between conventional B-mode frames. In a typical conventional ultrasound system having color Doppler capability, a flow image containing the flow information is superimposed on a conventional B-mode image output. In the resulting display, stationary tissue is depicted by a standard B-mode intensity value, while flowing fluid is depicted by red (for fluid flowing toward the probe) or blue (for fluid flowing away from the probe). The measured velocity at each location is typically indicated by a color saturation or luminance value, whereby low velocities are depicted by "dim" color and high velocities are depicted by "bright" color.

An alternative to color Doppler imaging, referred to in the art as power Doppler, power flow, or energy flow imaging, does not measure the direction or velocity of fluid flow. Rather, only the amount of Doppler energy in the echo signal is measured for each location in the target region. Thus, for a given location in the target plane receiving the sequence of "m" Doppler pulses, where the magnitude and phase of the reflections are given by a complex sequence $R(k)=\{R_1, R_2, R_3, \ldots, R_m\}$, the complex sequence $R(k)$ is high-pass filtered to remove effects of stationary tissues. The remaining signal represents the Doppler energy in the sequence $R(k)$. Conventional power Doppler systems display a flow image that is a monochromatic or color intensity image of this Doppler energy, the flow image being superimposed on a conventional B-mode display. As described in Zagzebski, supra, power Doppler systems are usually credited with being more sensitive to the presence of fluid flow as compared to color Doppler systems, while being generally insensitive to the actual velocity of the fluid flow. Other tradeoffs and comparisons between color Doppler and power Doppler modes are described in Zagzebski, supra.

One disadvantage of conventional Doppler systems (color Doppler or power Doppler) lies in their lack of frame rate and spatial resolution as compared to B-mode systems. While a typical B-mode system may have a frame rate of 30 frames/sec at a spatial resolution of 1024 lines at 1024 samples/line, the invocation of a Doppler feature can drop the frame rate to as low as 8 frames/sec, with the flow image being a mere 64 lines at 64 samples/line. It is to be appreciated that these parameters are presented by way of example only in order to illustrate certain aspects of the prior art, and are not intended to limit the scope of the preferred embodiments disclosed infra. A primary reason for the low frame rate and resolution for Doppler systems lies in the substantial number of data samples needed per location to get acceptable velocity measurement accuracy. The number of data samples per location corresponds to the number of pulses (vectors) that need to be sent down a given line during Doppler frame acquisition. According to the uncertainty principle, the frequency shift cannot be detected accurately when the observation period is short. Although interleaving schemes known in the art (e.g., fire vector 1 for line 1, vector 1 for line 9, vector 2 for line 1, etc.) can increase the time spacing between vectors without decreasing the frame rate, there is still a substantial number of vectors needed per line (e.g., 24) to get acceptable frequency shift (i.e., velocity)

measurements. Each vector needs a dedicated round-trip time from the probe, a 10-cm trip in a typical scenario. Using the speed of sound at 13 $\mu$s/cm, then the Doppler frame acquisition time is equal to (13 $\mu$s/cm)(10 cm/vector)(64 lines/frame)(24 vectors/line)=199.7 ms/frame. And, as stated supra, this all needs to take place between B-frames, resulting in very low overall frame rates. Furthermore, although the frame rate may be increased by decreasing the number of samples per location or by decreasing the number of locations considered, lower resolution and/or velocity accuracy will result.

Another problem found in conventional Doppler systems relates to clutter. Clutter signals, sometimes referred to as flash artifacts, are undesirable Doppler signals that arise from structures and targets in the body that do not represent fluid flow but which nevertheless may have Doppler shifts. Clutter signals may be caused by slow tissue or vessel wall motion arising from heart beats, arterial pulsations, or respiration. Clutter signals can also arise due to movement of the transducer by the operator. These unwanted signals are typically filtered out, so that the flow image only represents true fluid flow and suppresses clutter. Clutter signals that have not been adequately suppressed are subsequently confused with flow signals, and are typically seen in the flow image as color displayed outside of regions where there is fluid flow, i.e., where it is anatomically implausible. As described below, however, conventional prior art methods of suppressing clutter signals can cause substantial distortions in the measured fluid velocity.

FIG. 1 shows a block diagram of a conventional Doppler system 100 designed to have Doppler capability as well as B-mode capability. Doppler system 100 comprises a transducer 102 that sequentially introduces B-mode frames and Doppler frames into a target region and receives B-mode echo frames and Doppler echo frames therefrom. As discussed supra, the Doppler frames are typically limited to a smaller target region than the B-mode frames. A front end processor 104 performs preliminary processing on the data as described in Ser. No. 09/493,969, supra, including digitization of the received signal, referred to as the RF signal, into a digitized RF signal x(k) at a sampling frequency $F_s$. Doppler system 100 further comprises a prior art demodulator 106 that receives the RF signal x(k) and demodulates it from its carrier frequency $F_c$ into component baseband signals I(k) and Q(k), where I(k) is the in-phase component and Q(k) is the quadrature phase component, and where the complex baseband signal $A(k)e^{j\phi(k)}$ is equal to I(k)+jQ(k).

Prior art demodulator 106 comprises a local oscillator 116, mixers 118 and 120, and low pass filters 122 and 124. Local oscillator 116 generates sinusoids at a mixing frequency $F_x$ that are in quadrature phase with each other, e.g., $\cos(2\pi F_x k)$ and $\sin(2\pi F_x k)$. Mixers 118 and 120 multiply the digitized RF signal x(k) with the quadrature-phase sinusoids, and the products are sent to low-pass filters 122 and 124, respectively. Disadvantageously, low-pass filters 122 and 124 are required to have sharp rolloffs at an upper frequency limit for proper mirror-canceling effect, which in practicality creates large group delay distortion, ringing, and other effects that compromise the quality and accuracy of the signals I(k) and Q(k).

For purposes of clarity, and not by way of limitation, the following notational explanations and clarifications are presented for use in the present disclosure. The notational representation $A(k)e^{j\phi(k)}$=I(k)+jQ(k) of the data stream appearing at the output of demodulator 106 would, of course, have a continuous-time representation of $A(t)e^{j\phi(t)}$, where $t=kT_s$ and $T_s=F_s$. A particular data sample $A(k_0)e^{j\phi(k_0)}$ at time $k_0$ represents the magnitude and phase of the demodulated ultrasound echo signal for a particular point $(x_0,y_0)$ in the target region for a particular frame number "$n_0$" in the sequence of interrogating frames. The phase $\phi(k_0)$ is the phase as measured against the phase of the interrogating pulse sent down the line of the sample point $(x_0,y_0)$. There exists a one-to-one mapping between each value of "k" and an index set (x,y,n), where "x" and "y" are target locations and "n" is the frame number. If a coordinate system is chosen such that the "x" dimension is orthogonal to the direction of the interrogating pulse, and such that the "y" direction is parallel to the direction of the interrogating pulse, then temporally adjacent samples at indices $k_0$ and $(k_0+1)$ correspond to spatially adjacent samples at indices $(x_0,y_0,n_0)$ and $(x_0,y_0+n_0)$ for the frame $n_0$, as summarized in Eqs. (1) and (2) below:

$$A(k_0)e^{j\phi(k0)}=A(x_0, y_0, n_0)e^{j\phi(x0,y0,n0)} \quad \{1\}$$

$$A(k_0+1)e^{j\phi(k0+1)}=A(x_0, y_0+1,n_0)e^{j\phi(x0,y0+1,n0)} \quad \{2\}$$

For purposes of the present disclosure, it is to be appreciated that the data stream $A(k)e^{j\phi(k)}$=I(k)+j Q(k) may be temporally cached and rearranged as needed for subsequent processing using methods known in the art. For example, instead of sequentially transmitting samples for $(x_0,y_0,n_0)$, $(x_0,y_0+1,n_0)$, $(x_0,y_0+2,n_0)$, , etc. down a particular data path, which corresponds to the original order $k_0$, $k_0+1$, $k_0+2$, etc. received temporally from of the demodulator 106, the data samples may be rearranged such that they are sent in frame-sequential order for a fixed target location, i e., in the order $(x_0,y_0,n_0)$, $(x_0,y_0,n_0+1)$, $(x_0,y_0,n_0+2)$, etc. Circuitry for accomplishing such rearrangement is known in the art and, unless otherwise indicated, is presumed to be present as required to permit the disclosed functionality to proceed.

Further, for purposes of clarity of disclosure, when data corresponding to sequential ultrasound frames at a fixed location (x, y) is presented, the following notation shall be used herein:

$$A(x,y,n)e^{j\phi(x,y,n)}=A_{xy}(n)e^{j\phi xy(n)} \quad \{3\}$$

$$I(x,y,n)=I_{xy}(n) \quad \{4\}$$

$$Q(x,y,n)=Q_{xy}(n) \quad \{5\}$$

Finally, it is to be appreciated that in conventional ultrasound systems having Doppler capability, the Doppler frames are generally processed separately from the B-mode frames after being demodulated by demodulator 106. In particular, the B-mode frames and Doppler frames are generally treated as separate sequences. For clarity of disclosure, and unless otherwise indicated, the counter variable "$n_B$" shall be used for B-mode frame data, while the counter variable "$n_D$" shall be used for Doppler frame data.

Doppler system 100 of FIG. 1 further comprises an amplitude detector 108 coupled to the output of demodulator 106. As described supra, caching and rearranging circuitry (not shown) is used to extract B-mode frames only from the output of demodulator 106 for input to the amplitude detector 108. For each target region location (x,y), amplitude detector 108 detects the amplitude $A_{xy}(n_B)$, the result representing the B-mode intensity value for that location. The result is then sent to an ultrasound display device.

Doppler system 100 further comprises wall filters 110 and 112, as well as a velocity estimator 114, for generating a flow image. As described supra, caching and rearranging circuitry (not shown) is used to extract Doppler frames only from the output of demodulator 106 for input into the wall filters 110 and 112. Wall filter 110 receives, for each location (x,y), the signal $I_{xy}(n_D)$ and filters that data stream framewise, i.e., with respect to the counter $n_D$. Wall filter 112 performs a similar filtering for the data stream $Q_{xy}(n_D)$. Wall filters 110 and 112 are similar to notch filters having a notch at the DC frequency, for filtering out the effects of slow-moving clutter. Velocity estimator 114 receives the outputs $I_{wxy}(n_D)$ and $Q_{wxy}(n_D)$ from the wall filters 110 and 112, respectively. From these sequences, velocity estimator 114 computes a phase sequence $\phi_{xy}(n_D)$ and, as known in the art, proceeds to compute a fluid flow velocity as being proportional to the derivative $d\phi_{xy}/dn_D$ at that location. Further information on Doppler systems similar to the Doppler system 100 can be found in U.S. Pat. No. 5,228,009 to Forestieri et. al., which is incorporated by reference herein.

Several disadvantages are incurred by the Doppler system 100 of FIG. 1. As described supra, several Doppler frames (for example, 8 to 16 frames) must be transmitted between B-mode frames, substantially slowing down the overall frame rate, forcing poor flow image resolution, and forcing small area coverage for the flow image. Furthermore, because the wall filters 110 and 112 can only operate on a stream 8 to 16 samples of data (the number of Doppler frames sent between B-mode frames), a high degree of frequency leakage and distortion is introduced, causing either a high degree of insensitivity or, alternatively, a high degree of clutter artifacts to be present in the flow image. Even further, substantial inaccuracy in the phase angle $\phi_{xy}(n_D)$, and therefore the measured flow velocity, is introduced by virtue of the separate wall-filtering of the in-phase component $I_{xy}(n_D)$ and the quadrature phase component $Q_{xy}(n_D)$ prior to computation of the phase angle $\phi_{xy}(n_D)$.

It has been found that certain medical procedures would be made easier and more effective if real-time ultrasound images could be provided that identify areas of fluid flow in a target region with a high spatial resolution. As an example, during a breast biopsy procedure a probe needle is inserted into a woman's breast for extracting sample tissue from a suspicious lesion. It would be desirable to provide a high-resolution flow image which, when superimposed on a B-mode image, could be used to help guide the needle to the lesion without puncturing veins or arteries in the breast.

It has been found that the conventional Doppler system 100 yields a frame rate that is too slow and a flow image resolution that is too low for medical applications such as the above biopsy application. Additionally, there is often a temporal mismatch between the B-mode image and the flow image because of the different processing times needed. In addition to being disadvantageous in the above biopsy application, this temporal mismatch is also disadvantageous in cardiology applications where the valve movement of heart is mismatched with the fluid flow image of the blood moving through the heart.

FIG. 2 shows an ultrasound system 200 which represents a prior art design for generating a flow image from B-mode ultrasound frames. Imaging system 200 comprises a transducer 202 and front end processor 204 similar to the transducer 102 and front end processor 104 of FIG. 1. Ultrasound system 200 further comprises a demodulator 206 similar to the demodulator 106 of FIG. 1, with elements 216–224 operating in a similar manner to elements 116–124 respectively, of FIG. 1. Ultrasound system 200 further comprises an amplitude detector 208 for generating B-mode image data that is similar to amplitude detector 108 of FIG. 1. However, instead of using separate Doppler frames between B-mode frames to detect fluid flow, ultrasound system 200 attempts to derive flow information from the B-mode frames themselves. In particular, ultrasound system 200 comprises an amplitude change detector 210 coupled to receive amplitude values $A_{xy}(n_B)$ from the amplitude detector 208 and to generate flow image values based on changes in the amplitude values across multiple frames. Ultrasound system 200 operates based on the theoretical principal that, for a given location in the target region, small changes in B-mode intensity between frames will occur if there is fluid flow at that location. Descriptions of various prior art designs that use changes in B-mode amplitude between frames to detect fluid flow can be found in U.S. Pat. No. 5,980,459 to Chiao et. al., which is incorporated by reference herein.

The prior art ultrasound system 200, however, is difficult to implement in practice because the B-mode intensity for fluid regions is already very small (i.e., fluid such as blood has a small acoustic reflectivity compared to the surrounding tissue), and amplitude changes between frames due to fluid flow are even smaller. The resulting flow image is often too noisy for practical use. Additionally, because of the disadvantages of prior art demodulator 206 as described in Ser. No. 09/493,969, supra, inter-frame amplitude comparisons can be inconsistent because the amplitude measurements themselves may be subject to group delay distortion and other adverse effects, further degrading the flow image.

Accordingly, it would be desirable to provide an ultrasound imaging system capable of processing B-mode ultrasound frames to derive flow information in addition to B-mode intensity information for a target region.

It would be further desirable to provide such an ultrasound system yielding a flow image with a high frame rate and with a spatial resolution as great the B-mode image resolution.

It would be still further desirable to provide such an ultrasound system in which the flow image is robust against clutter effects, such that the presence or absence of fluid flow at a given location is readily and reliably perceived by a user.

It would be still further desirable to provide such an ultrasound system in which there is minimal temporal mismatch between the B-mode image and the flow image.

It would be even further desirable to provide an ultrasound system that can be adapted to generate accurate flow velocity information for very slow moving fluids moving slower than a predetermined maximum velocity.

It would be still further desirable to provide such an ultrasound system that is relatively inexpensive to implement, easy to use, and easy to adjust for optimal flow image output.

SUMMARY

According to a preferred embodiment, an ultrasound imaging system is provided in which B-mode echo frames are used to derive phase information for each location in a target region, wherein changes in the phase information across multiple frames is processed for detecting the presence of fluid flow at that location. A demodulator receives the B-mode echo frames and demodulates them into baseband signal components (e.g., in-phase and quadrature components), and the phase information is derived therefrom. In accordance with a preferred embodiment, the demodulator should be highly accurate and robust, such that frame-to-frame change in the phase information is reliably measured for a given target location. From the reliably measured phase information, a phase shift metric is then computed and compared to a first threshold value. Flow is determined to be present if the phase shift metric is greater than the first threshold value, and is determined to be absent otherwise. If flow is detected, the flow image is set to a constant value for that location, and is set to a null value otherwise. Alternatively, if flow is detected, the flow image may be set to a different non-null value, such as a color value modulated by the B-mode intensity at that location. The user may adjust the first threshold value in real time through an input device, such as a knob or keyboard, to increase or decrease the flow sensitivity as desired and/or to eliminate the slow-moving clutter.

In a preferred embodiment, the phase shift metric is computed for each location by forming a difference sequence from the phase information, averaging the difference sequence, computing the absolute value of the averaged difference sequence, and then filtering the result with a contrast-preserving temporal filter. The contrast-preserving temporal filter is a time-varying, first order, infinite impulse response filter designed to have a fast attack time during a systolic cycle period and a slow decay time during a diastolic cycle period. Prior to comparison with the threshold value, the phase shift metric may be averaged with that of neighborhood locations in the target region.

For additional clutter removal, the flow image value at a target location may be further modified depending on the B-mode image value at that location. In accordance with a preferred embodiment, the B-mode image value is compared to a lower threshold value and an upper threshold value. If the B-mode image value is greater than the upper threshold value, then the flow image value is reset to null, because that location likely represents a slow-moving object such as a vessel wall. If the B-mode image value is less than a lower threshold value, then the flow image value is also reset to null, because that location likely represents noise. If the flow image value was already a null value, no B-mode image value comparison is performed and the B-mode image value is displayed for that pixel.

In an optional mode of operation in which fluid flow is assumed to be very slow, i. e., less than a predetermined Nyquist velocity, the phase information may be conventionally processed to produce a color flow image indicating a measured fluid flow velocity. In this circumstance, the measured velocity is computed as being proportional to a first derivative of the temporal phase information.

Advantageously, especially when used in conjunction with the demodulator of parent application Ser. No. 09/493,969, an ultrasound imaging system according to the preferred embodiments provides a flow image that is as large as the B-mode image, has the same high frame rate as the B-mode image, has the same high resolution as the B-mode image, and is temporally and spatially matched to the B-mode image. The provided system is also robust against clutter effects, relatively inexpensive to implement, easy to use, and easy to adjust for optimal flow image output.

DETAILED DESCRIPTION

Figure 3:
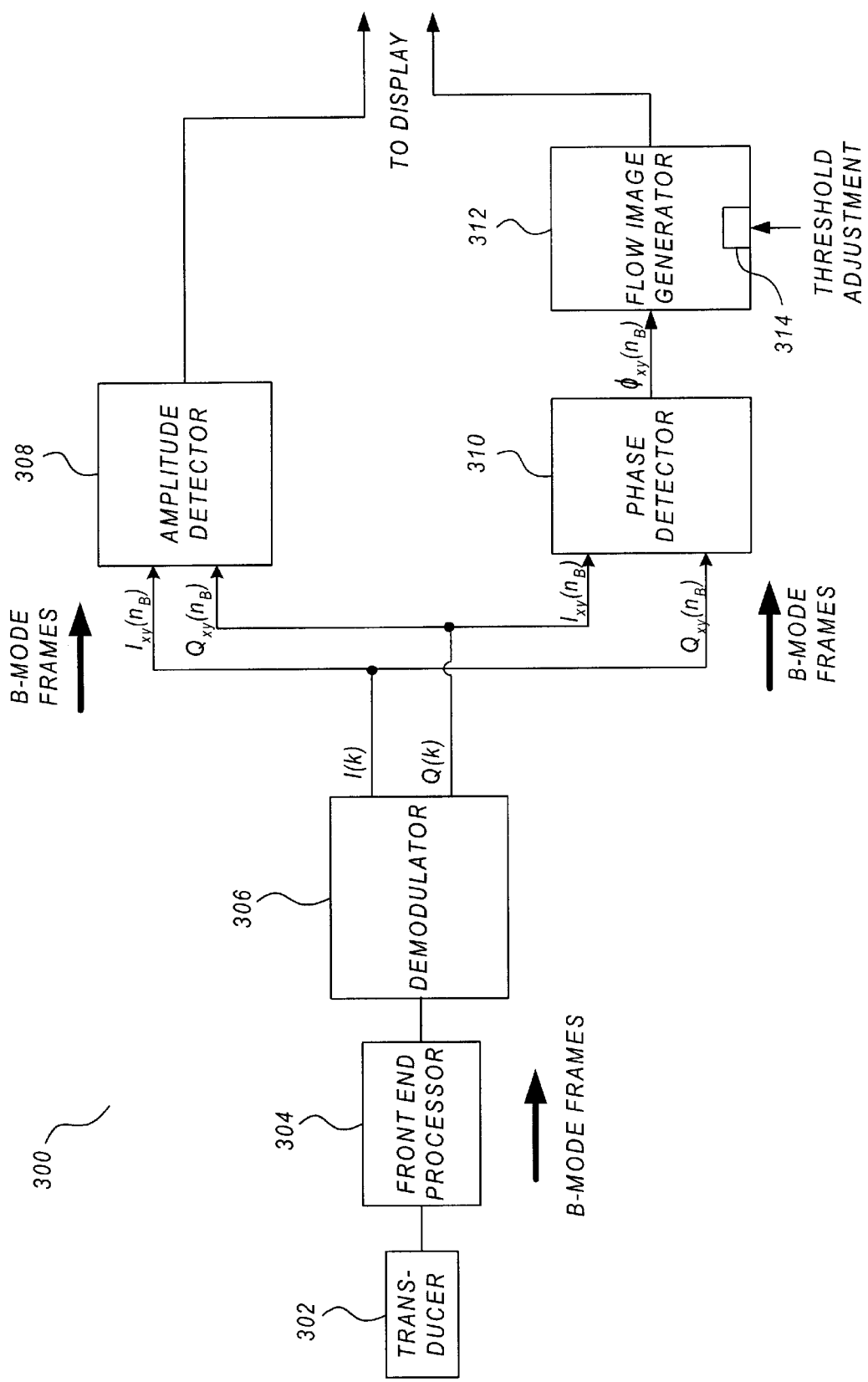
FIG. 3 shows an ultrasound imaging system in accordance with a preferred embodiment.

FIG. 3 shows an ultrasound imaging system 300 in accordance with a preferred embodiment. Ultrasound system 300 comprises a transducer 302 and a front end processor 304 similar to prior art transducers 202 and front end processor 204, supra. It is to be appreciated that while transducer 302 is to transmit interrogating B-mode frames and receive B-mode echo frames from the target region, the ultrasound system 200 may be used in conjunction with a variety of imaging modes other than B-mode yet still be within the scope of the preferred embodiments, provided that amplitude and phase information for each target location and each interrogating frame may be accurately and consistently derived therefrom.

Figure 1:
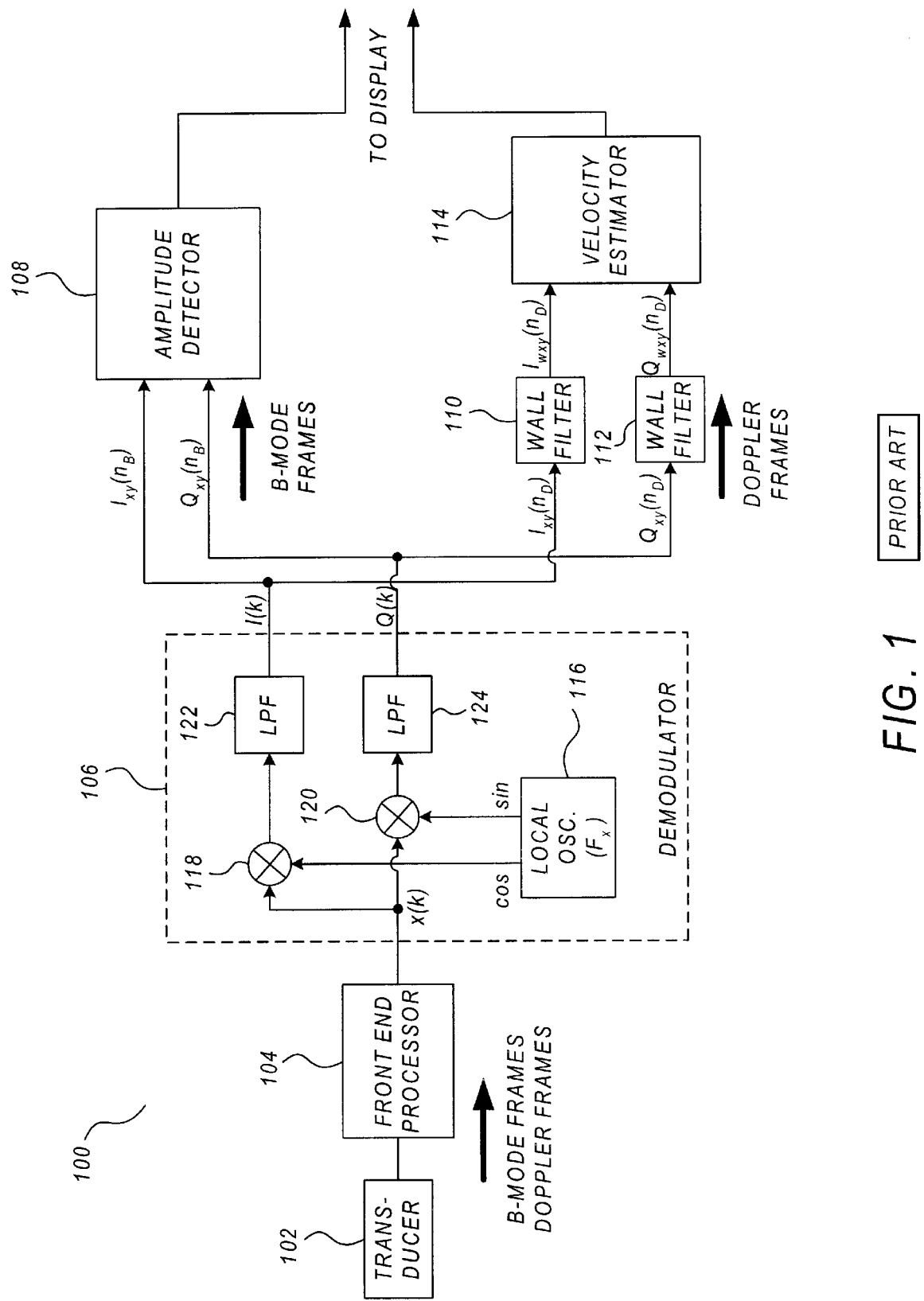
FIG. 1 shows a ultrasound system using dedicated Doppler frames to sense flow information in accordance with the prior art.
Figure 2:
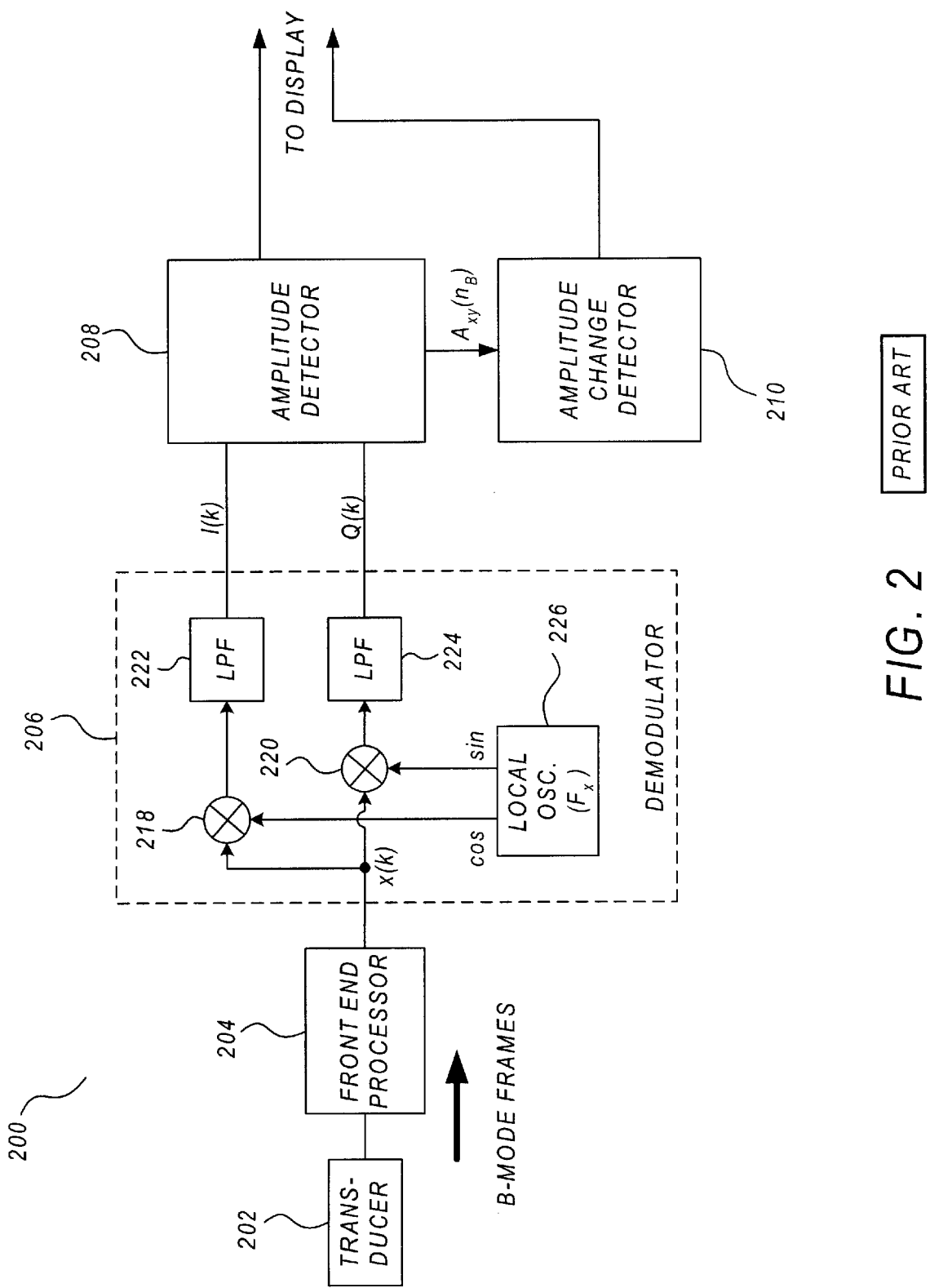
FIG. 2 shows an ultrasound system using B-mode frame-to-frame amplitude changes to sense flow information in accordance with the prior art.

Ultrasound system 300 further comprises a demodulator 306 for producing demodulated signal components, shown as in-phase component I(k) and quadrature phase component Q(k) in FIG. 3, from the digitized data stream x(k) provided by the front end processor 304. However, it would be within the scope of the preferred embodiments for demodulator 306 to produce any set of basis vectors from x(k) provided that amplitude and phase information may be derived therefrom. Preferably, demodulator 306 is similar to the demodulator disclosed in Ser. No. 09/493,969, supra, which is designed to provide highly reliable and consistent demodulated signals that are less subject to group delay and other distortion effects that prior art demodulators experience. However, in general, other demodulators may be used without departing from the scope of the preferred embodiments, provided that they provide highly accurate and consistent demodulated signals to the downstream components of the ultrasound system 300. For purposes of describing the remainder of ultrasound system 300, and as described supra with respect to the prior art systems of FIGS. 1 and 2, it is presumed that rearranging and caching circuitry (not shown) provides a reordering from the sequences I(k) and Q(k) into the sequences $I_{xy}(n_B)$ and $Q_{xy}(n_B)$ as necessary, where $n_B$ is the frame counter for the B-mode frames, and where $I_{xy}(n_B)$ and $Q_{xy}(n_B)$ denote the in-phase and quadrature phase components at the location (x,y) for frame $n_B$.

Ultrasound system 300 further comprises an amplitude detector 308 for receiving the signals $I_{xy}(n_B)$ and $Q_{xy}(n_B)$ and computing therefrom an amplitude signal $A_{xy}(n_B)$ in accordance with the relationship of Eq. (6), from which the B-mode intensity signal can be generated:

$$A_{xy}(n_B)=\sqrt{[I^2_{xy}(n_B)+Q^2_{xy}(n_B)]} \quad \{6\}$$

Ultrasound system 300 further comprises a phase detector 310 for receiving the signals $I_{xy}(n_B)$ and $Q_{xy}(n_B)$ therefrom an amplitude signal $A_{xy}(n_B)$ in accordance with the relationship of Eq. (7):

$$\phi_{xy}(n_B)=\arc\tan[Q_{xy}(n_B)/I_{xy}(n_B)] \quad \{7\}$$

Ultrasound system 300 further comprises a flow image generator 312 that generates a flow image $FLOW_{xy}(n_B)$ by detecting, for each location (x,y), changes in the phase $\phi_{xy}(n_B)$ across multiple frames and detecting the presence of fluid flow therefrom. The resulting flow image values FLOW$_{xy}$(n$_B$) are provided along with the B-mode image values A$_{xy}$(n$_B$) to an ultrasound display device (not shown). Flow image generator 312 is provided with threshold values derived from a user-adjustable input 314 for optimal generation of the flow image, as described infra. Because the phase detector 310 and flow image generator 312 operate on the same set of B-mode echo data as the amplitude detector 308, the ultrasound system 300 advantageously provides a flow image is as large as the B-mode image, has the same high frame rate as the B-mode image, has the same high resolution as the B-mode image, and is temporally matched to the B-mode image.

Figure 4:
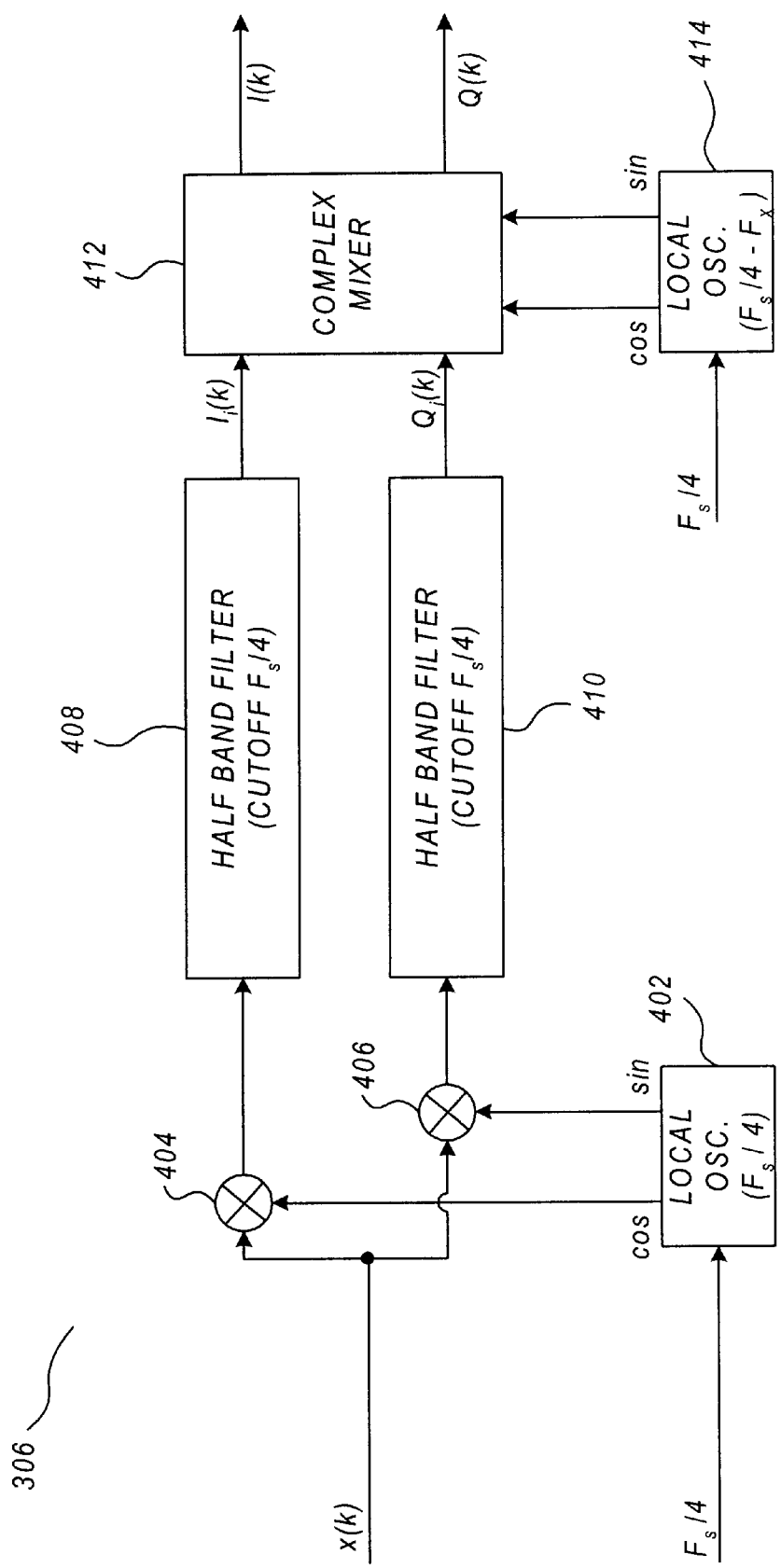
FIG. 4 shows a demodulator for use in the system of FIG. 3.

FIG. 4 shows a block diagram of demodulator 306 in accordance with a preferred embodiment. Demodulator 306 comprises a first stage local oscillator 402, mixers 404 and 406, half-band filters 408 and 410, a complex mixer 412, and a secondary local oscillator 414 coupled as shown in FIG. 4. Demodulator 306 comprises a quadrature mixing device formed by first stage local oscillator 402 and mixers 404 and 406 having a mixing frequency that is one quarter of the sampling frequency F$_s$, together with half-band filters 408 and 410 having a cutoff frequency equal to one quarter of the sampling frequency F$_s$. The outputs of half-band filters 408 and 410 are optimally mirror-canceled without the undesirable group delay and distortion effects experienced in prior art demodulators. The complex mixer 412 then rotates the outputs of the half-band filters 408 and 410 to the baseband to produce reliable and consistent signal components I(k) and Q(k). In one embodiment, secondary oscillator 414 generates a mixing frequency for the complex mixer 410 equal to one quarter of the sampling frequency F$_s$ minus the carrier frequency F$_c$ of the interrogating B-mode signals. In another embodiment, secondary oscillator 414 generates a mixing frequency for the complex mixer 410 equal to one quarter of the sampling frequency F$_s$ minus a swept frequency for even more optimal signal-to-noise performance. The operation of demodulator 306 is detailed more fully in Ser. No. 09/493,969, supra.

Figure 5:
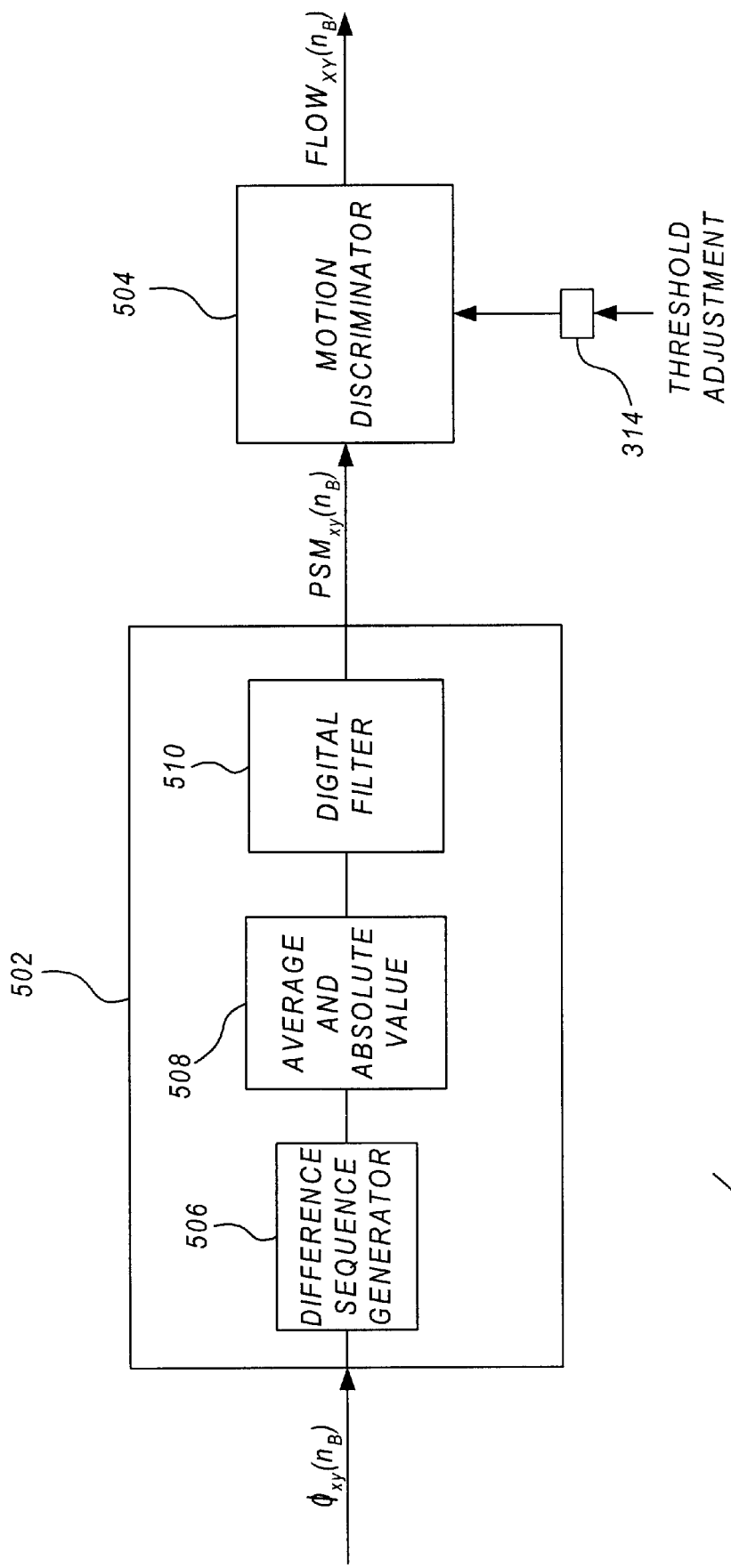
FIG. 5 shows a flow image generator for use in the system of FIG. 3.

FIG. 5 shows a block diagram of flow image generator 312 in accordance with a preferred embodiment. Flow image generator 312 comprises a phase discriminator 502 for generating a phase shift metric PSM$_{xy}$(n$_B$) from the detected phase sequence $\phi_{xy}$(n$_B$). Flow image generator 312 further comprises a motion discriminator 504 which receives the phase shift metric PSM$_{xy}$(n$_B$) as well as a user adjustable threshold value from a user input 314 and generates a flow image value PSM$_{xy}$(n$_B$) therefrom.

Phase discriminator 502 comprises a difference sequence generator 506, an average and absolute value generator 508, and a digital filter 510. Difference sequence generator 506 generates a difference sequence DIFF$_{xy}$(n$_B$) according to Eq. {8} below:

$$\mathrm{DIFF}_{xy}(n_B) = \phi_{xy}(n_B) - \phi_{xy}(n_B - 1) \quad \{8\}$$

While in a preferred embodiment the difference sequence is a first-order difference sequence, it would be within the scope of the preferred embodiments to generate alternative difference sequences, or difference sequences having weighted terms, to achieve a desired flow detection objective. By way of nonlimiting example, difference sequence generator 506 may be designed to produce a second-order difference sequence for imaging acceleration or deceleration of the fluid flow in the target region.

Average and absolute value generator 508 performs the prescribed functions of generating an average sequence from DIFF$_{xy}$(n$_B$) and taking the absolute value thereof to produce ADIFF$_{xy}$(n$_B$), as shown in Eq. (9):

$$\mathrm{ADIFF}_{xy}(n_B) = |[1/M][\mathrm{DIFF}_{xy}(n_B) + \mathrm{DIFF}_{xy}(n_B-1) + \ldots + \mathrm{DIFF}_{xy}(n_B - M+1)]| \quad \{9\}$$

Although the number of consecutive elements M of the sequence DIFF$_{xy}$(n$_B$) used to generate ADIFF$_{xy}$(n$_B$) may vary depending on system-specific parameters affecting sensitivity, it has been found that M=2 to 5 may provide a suitable averaging effect.

Digital filter 510 comprises a time varying, first order, infinite impulse response filter designed to have a fast attack time during a systolic cycle period and a slow decay time during a diastolic cycle period. In a preferred embodiment, digital filter 510 designed to have the transfer function indicated by Eq. {10};

$$H(z) = (1-p)\frac{z+1}{z-p} (0 < p < 1) \quad \{10\}$$

As indicated by Eq. (10), the digital filter 510 has a "pole" at p+j0 while having a "zero" at −1+j0, representing a low-pass filter and having an inverse exponential step response of the form C1(1−e$^{-jkC2}$) where C1 and C2 are positive constants readily computed from Eq. (10). In accordance with a preferred embodiment, the parameter "p" of the digital filter varies depending on the patient's heartbeat cycle. In particular, the value "p" is set to a lower value during a systolic cycle to provide a fast attack time, and is changed to a higher value during a diastolic cycle to provide a slower decay time. By way of example and not by way of limitation, a value p=0.8 may be used during the systolic cycle, while a value p=0.98 may be used during the diastolic cycle. Using these values and other typical system values, the digital filter 510 would be fast-attacking during the systolic cycle, achieving 90% of its steady state response after about 25 ms, while the digital filter 510 would be slow-decaying during a diastolic cycle, decaying 90% toward its steady state response after about 140 ms. In operation, the systolic cycle is present whenever the fluid velocity is increasing frame over frame, whereas the diastolic cycle is present whenever the fluid velocity is decreasing frame over frame. Therefore, according to a preferred embodiment, the value for "p" is determined on a per-location basis. The value DIFF$_{xy}$(n$_B$) can be used as an indicator of relative frame-to-frame fluid velocity for determining the presence of the systolic versus the diastolic cycle. The output of digital filter 510 constitutes the output of the phase discriminator 502, i.e., the phase shift metric PSM$_{xy}$(n$_B$).

Motion discriminator 504 receives the phase shift metric PSM$_{xy}$(n$_B$) from the phase discriminator 502 and computes a flow image value FLOW$_{xy}$(n$_B$) therefrom for output to an ultrasound display device. In particular, motion discriminator 504 thresholds PSM$_{xy}$(n$_B$) by a threshold value that remains fixed unless changed by the user at user input 314. In a preferred embodiment, the flow image value FLOW$_{xy}$(n$_B$) is set to a constant non-null value if the threshold is exceeded, and is set to a null value otherwise. The constant non-null value corresponds to a constant color and brightness on the output display that distinguishes to the user the presence of flow from the rest of the B-mode display, e.g., to a bright green value. The null value corresponds to no output at all for the flow image, that is, the user simply sees the standard B-mode image for that location. It has been found that the use of a simple user-adjustable threshold, adjustable by the user in real time as he or she views the ultrasound display, is a good way to eliminate clutter or other spurious signals while still providing for a fast, real time, high-resolution flow image indicating the presence of fluid flow. As described supra, one advantageous use of such an ultrasound flow image display would be for guiding, in real time, a biopsy needle into a patient so that arteries or other sensitive areas of flow are avoided by the needle. In an alternative preferred embodiment, a spatially local region of values for $FLOW_{xy}(n_B)$ may be averaged together (e.g., a 3×3 region) prior to the thresholding step.

In an alternative preferred embodiment, the flow image values $FLOW_{xy}(n_B)$ are not required to binary ("on/off") in nature. Instead, when the presence of fluid flow is detected, the flow image value may communicate other information as well. By way of nonlimiting example, when the presence of fluid flow is detected, the value $FLOW_{xy}(n_B)$ may be a distinctive color whose intensity or brightness is modulated by the B-mode intensity value at that location. By way of further nonlimiting example, when the presence of fluid flow is detected, the intensity or brightness may be modulated by an actual measured fluid velocity. Although in most circumstances this measured fluid velocity will be highly aliased as discussed infra, this information might still be useful in comparing relative flow velocities at adjacent image locations.

Figure 6:
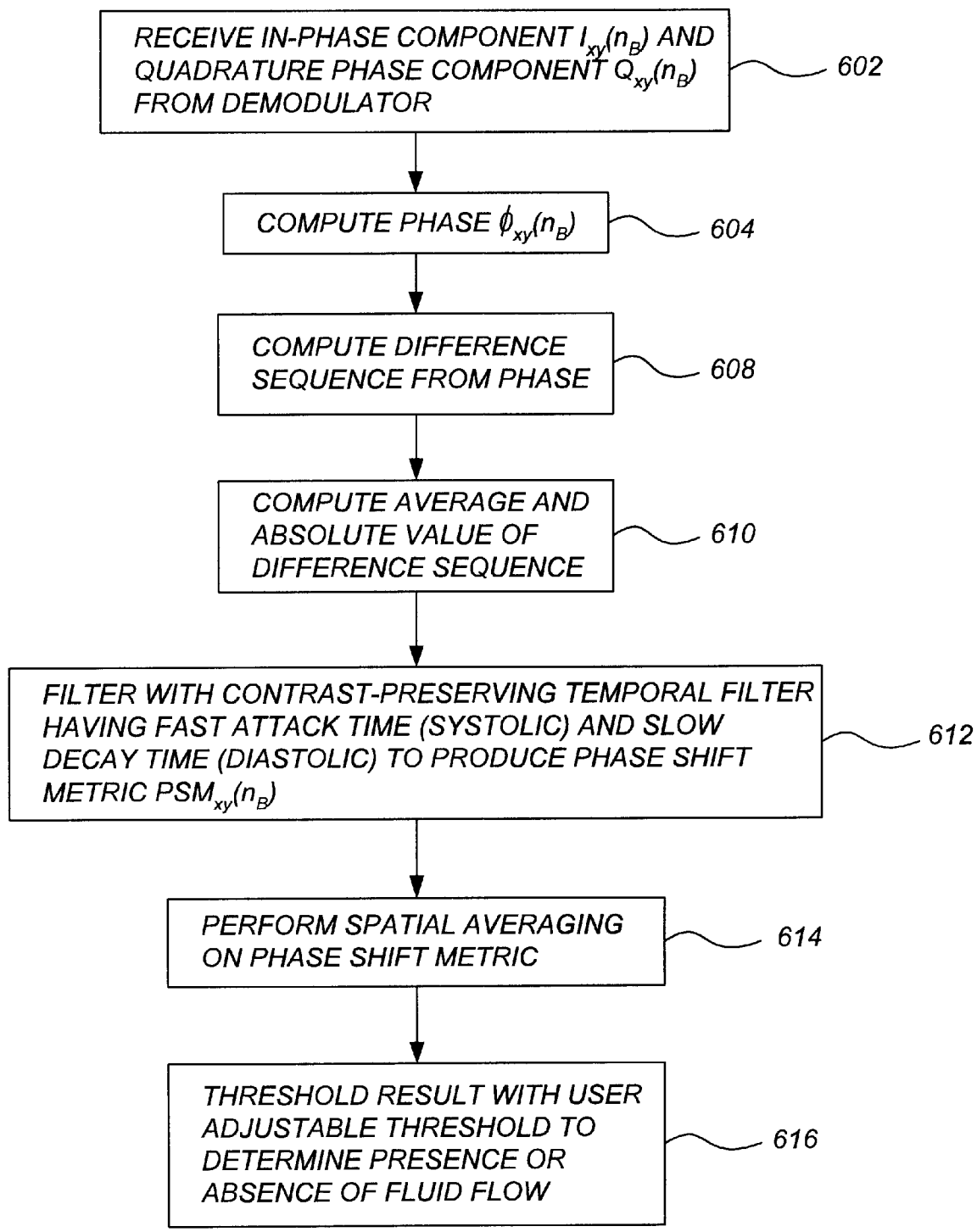
FIG. 6 shows steps for generating a flow image using B-mode data in accordance with a preferred embodiment.

FIG. 6 shows steps for generating a flow image using B-mode data in accordance with a preferred embodiment. At step 602, in-phase component $I_{xy}(n_B)$ and quadrature phase component $Q_{xy}(n_B)$ are received from the demodulator. At step 604, the phase information is computed from these components. At step 608, a difference sequence is computed from the phase sequence. At step 610, an average difference sequence is computed from the difference sequence by averaging each element with at least one neighboring element, and each resulting element in the average difference sequence is replaced with its absolute value. At step 612, the average difference sequence is filtered with a contrast-preserving filter. Optionally, at step 614, spatially neighboring elements within a frame may be averaged together. Finally, at step 616, the result is compared to a user-adjustable threshold to determine the presence of absence of fluid flow.

Figure 7:
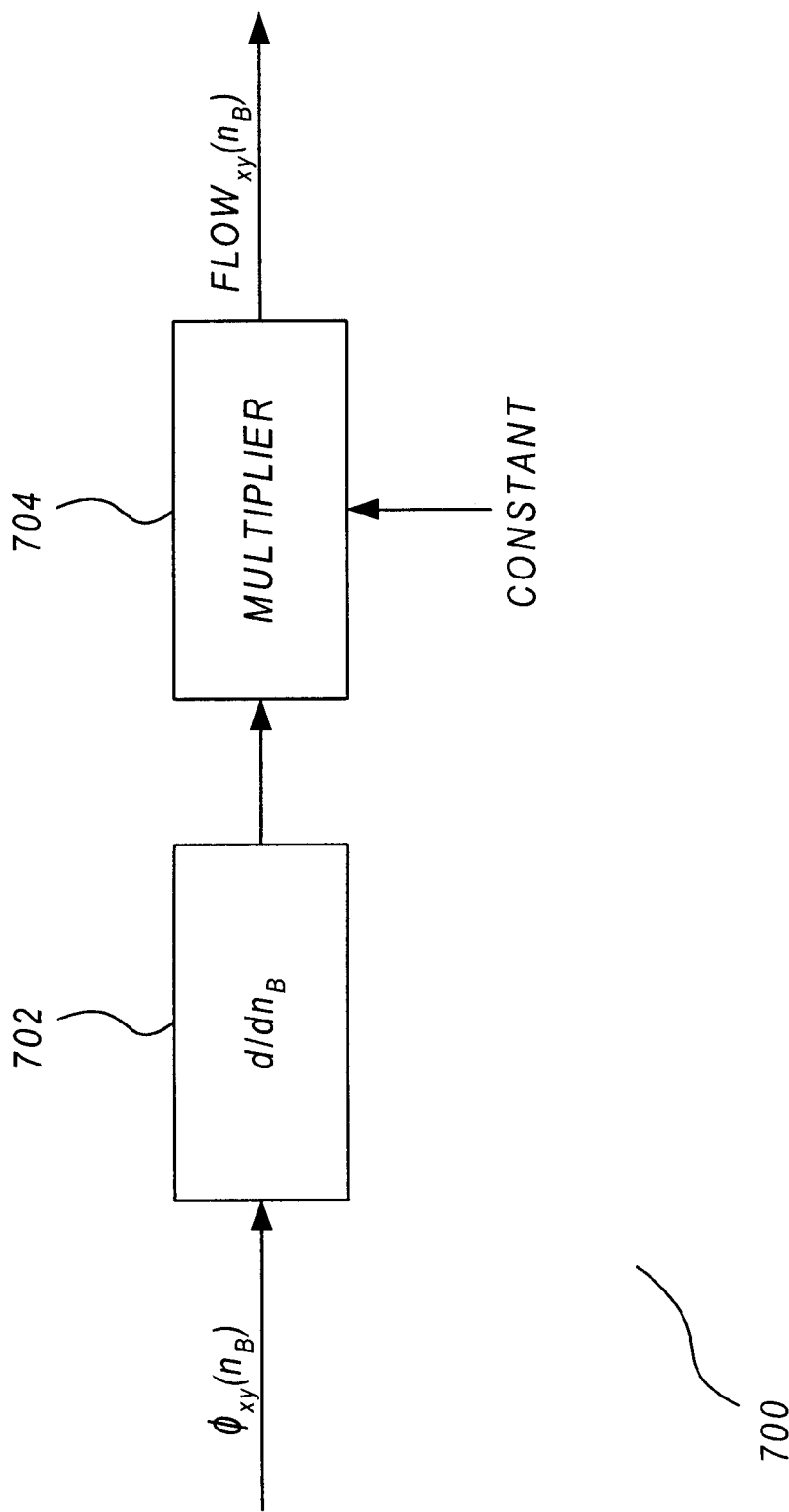
FIG. 7 shows an alternative flow image generator for use in the system of FIG. 3.

FIG. 7 shows a velocity estimator 700 in accordance with an alternative preferred embodiment. Velocity estimator 700 may be used instead of the flow image generator 312 of FIG. 5, or it may exist in conjunction with the flow image generator 312 whereby a user may use a mode switch to switch between the velocity estimator 700 or the flow image generator 312. Velocity estimator 700 comprises a differentiator 702 and multiplier 704 for providing a scaled first derivative of the phase $\phi_{xy}(n_B)$, operating in accordance with principals known in the art to provide a velocity estimation. Because the B-mode vector acquisition rate is relatively low compared to the conventional color Doppler mode, the velocity estimator 700 will only produce valid non-aliased samples for very low fluid velocities. Nevertheless, this may provide a non-aliasing display for certain low-speed flow applications requiring high spatial resolution, when the velocity is known to be less than a Nyquist velocity as given by Eq. (11):

$$V_{Nyquist} = \frac{F_B C}{2 F_c \cos \theta_d} \quad \{11\}$$

In the above Eq. (11), $F_B$ represents the B-mode frame rate, C represents the speed of sound in the target image, $F_c$ represents the B-mode carrier frequency, and $\theta_d$ represents the Doppler angle between the fluid flow direction and the direction of the interrogating pulse. By way of nonlimiting example, assuming a Doppler angle of zero and parameter values FB=15 Hz, C=1540 m/s, and Fc=2 MHz, the Nyquist velocity computes to $V_{Nyquist}$=5.775 mm/s. If the fluid flow is known to be below this velocity, then the output of the velocity estimator 700 of FIG. 7 will be accurate and non-aliased.

Figure 8:
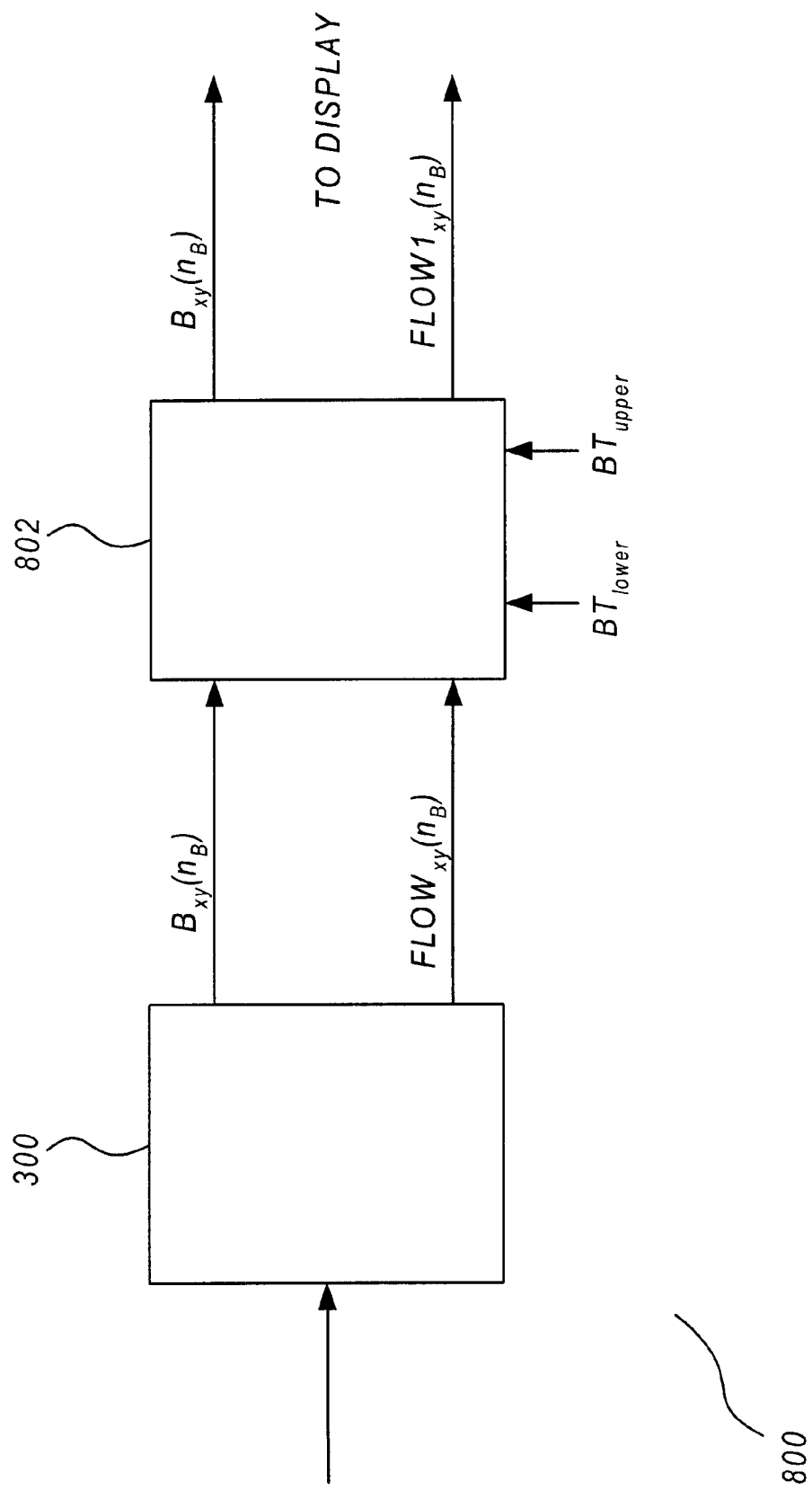
FIG. 8 shows an ultrasound imaging system.

FIG. 8 shows an ultrasound imaging system 800 in accordance with a preferred embodiment. Ultrasound imaging system 800 comprises the ultrasound system 300 as shown in FIG. 3, supra, as well as a selective flow image suppressor 802 coupled to receive the B-mode image value $B_{xy}(n_B)$ and flow image value $FLOW_{xy}(n_B)$ therefrom. Flow image suppressor 802 uses the value of $B_{xy}(n_B)$, a predetermined lower threshold value $BT_{lower}$, and a predetermined upper threshold value $BT_{upper}$ to selectively suppress the flow image for additional clutter removal. In particular, $B_{xy}(n_B)$ is compared $BT_{lower}$ and $BT_{upper}$. If $B_{xy}(n_B)$ >$BT_{upper}$ then $FLOW_{xy}(n_B)$ is reset to null, because that location likely represents a stationary tissue or slow-moving object such as a vessel wall. If $B_{xy}(n_B)$<$BT_{lower}$ then $FLOW_{xy}(n_B)$ is also reset to null, because that location likely represents noise. If the flow image value was already a null value, no B-mode image value comparison is performed by flow image suppressor 802. The values of parameters $BT_{lower}$ and $BT_{upper}$ may be dynamically adjusted to produce a clutter-reduced flow image. In one preferred embodiment, the values $BT_{lower}$ and $BT_{upper}$ may be dynamically user-adjustable. In an alternative preferred embodiment, $BT_{lower}$ and $BT_{upper}$ may be automatically adjusted through a feedback process that dynamically computes a clutter metric and continually adjusts $BT_{lower}$ and $BT_{upper}$ to minimize that metric.

Whereas many alterations and modifications of the present invention will no doubt become apparent to a person of ordinary skill in the art after having read the foregoing description, it is to be understood that the particular embodiments shown and described by way of illustration are in no way intended to be considered limiting. For example, the preferred embodiments are compatible with multi-zone transmit and receive focusing imaging. As a further example, the operations performed by flow image generator 312 may also be adapted for use in conventional color Doppler imaging systems. Therefore, reference to the details of the preferred embodiments are not intended to limit their scope, which is limited only by the scope of the claims set forth below.

What is claimed is:

1. A method for imaging fluid flow in a target region, comprising the steps of:
   transmitting a sequence of B-mode interrogating frames into the target region;
   receiving from the target region a sequence of B-mode echo frames corresponding to the sequence of B-mode interrogating frames;
   processing each B-mode echo frame to derive phase information for each location in the target region; and
   for each location in the target region, detecting changes in the phase information across multiple B-mode echo frames for detecting the presence of fluid flow at that location.

2. The method of claim 1, further comprising the steps of:
   deriving a B-mode output image for each B-mode echo frame, the B-mode output image comprising, at each location of the target region, an intensity value corresponding to an echo amplitude at that location;
   deriving a flow image for each B-mode echo frame, the flow image comprising, at each location of the target region, a flow image value corresponding to fluid flow at that location; and providing said flow image and said B-mode output image to an ultrasound display device;

wherein said flow image and said B-mode output image have a substantially identical frame rate and a substantially identical spatial resolution.

3. The method of claim 2, said step of deriving a flow image comprising the steps of:

computing a phase shift metric from the detected changes in phase information across multiple B-mode echo frames;

comparing the phase shift metric with a first threshold value; and if the phase shift metric is less than the first threshold value, setting the flow image value to a null value.

4. The method of claim 3, said step of deriving a flow image further comprising the step of, if the phase shift metric is greater than the first threshold value, setting the flow image value to constant non-null value for indicating the presence of flow at that location.

5. The method of claim 3, said step of deriving a flow image further comprising the step of, if the phase shift metric is greater than the first threshold value, setting the flow image value to color-coded identifier that corresponds to a B-mode echo amplitude at that location.

6. The method of claim 3, further comprising the step of selectively suppressing the flow image value at each location according to said B-mode echo amplitude by performing the steps of:

comparing said B-mode echo amplitude to a predetermined lower threshold;

if said B-mode echo amplitude is lower than said lower threshold, resetting said flow image value to said null value;

comparing said B-mode echo amplitude to a predetermined upper threshold;

if said B-mode echo amplitude is higher than said predetermined upper threshold, resetting said flow image value to said null value.

7. The method of claim 3, said step of processing each B-mode echo frame to derive phase information yielding, for each location in the target region, a temporal sequence of phase values, and wherein, for that location, said step of computing a phase shift metric comprises the steps of:

computing a difference sequence from the temporal sequence of phase values, the difference sequence corresponding to the difference between adjacent elements of the temporal sequence of phase values;

computing an average difference sequence from the difference sequence by averaging each element therein with at least one neighboring element;

replacing each element in the average difference sequence with its absolute value;

filtering the average difference sequence with a contrast-preserving temporal filter; and setting the phase shift metric equal to an output of the contrast-preserving temporal filter.

8. The method of claim 7, wherein said contrast-preserving temporal filter comprises a time-varying, first order, infinite impulse response filter designed to have a fast attack time during a systolic cycle period and a slow decay time during a diastolic cycle period.

9. The method of claim 3, wherein a user may dynamically adjust the first threshold value to optimize the resulting flow image.

10. The method of claim 8, wherein for each location in the target region, said step of comparing the phase shift metric with a first threshold value comprises the steps of:

spatially averaging the phase shift metric with that of neighboring locations in the target region; and comparing the spatial average to the first threshold.

11. An apparatus for processing ultrasound signals, comprising:

a demodulator for receiving a sequence of frames of pulse-echo ultrasound data corresponding to pulse-echo ultrasound reflections received from a target region, said demodulator being adapted to generate, for each location in the target region and for each frame, a plurality of component baseband signals from which amplitude and phase information may be derived;

an amplitude detector coupled to receive said component baseband signals from said demodulator, said amplitude detector for computing, for each location in the target region and for each frame, an amplitude signal from said component baseband signals;

a phase detector coupled to receive said component baseband signals from said demodulator, said phase detector for computing, for each location in the target region and for each frame, a phase signal from said component baseband signals;

a phase discriminator coupled to receive said phase signals from said phase detector, said phase discriminator being adapted to generate, for each location in the target region, a phase difference metric corresponding to differences in said phase signals across a plurality of frames;

a motion discriminator coupled to receive said phase difference metrics from said phase discriminator, said motion discriminator being adapted to threshold said phase difference metrics by a predetermined threshold to determine the presence or absence of fluid flow at each location in the target region, said motion discriminator generating an output for each location in the target region equal to a null value in the absence of fluid flow and equal to a non-null value in the presence of fluid flow; and an output device for providing said amplitude signal and said motion discriminator output to an ultrasound display device, whereby a user may perceive a pulse-echo amplitude display having a fluid flow display superimposed thereon.

12. The apparatus of claim 11, wherein said pulse-echo ultrasound data corresponds to B-mode signals, wherein said amplitude signals are B-mode intensity signals, wherein said pulse-echo amplitude display is a B-mode display, and wherein said fluid flow display has a spatial resolution similar to a spatial resolution of said B-mode display.

13. The apparatus of claim 12, wherein said component baseband signals comprise an in-phase component and a quadrature component.

14. The apparatus of claim 13, further comprising an input device for allowing the user to dynamically adjust said predetermined threshold value for optimizing discrimination between the presence and absence of fluid flow.

15. The apparatus of claim 14, wherein said non-null value is set equal to a constant value, whereby said fluid flow display is a binary display indicating the presence or absence of fluid flow at each location in the target region.

16. The apparatus of claim 15, wherein said phase discriminator comprises:

a difference sequence generator for generating, for each location in the target region, a difference sequence corresponding to the difference between phase signals of temporally adjacent frames at that location;

a temporal averaging device for computing an average difference sequence from said difference sequence;

an absolute value generator for computing the absolute value of said average difference sequence;

a digital filter for filtering said absolute value of said average difference sequence, said digital filter being a contrast-preserving temporal filter; and a spatial averaging device for spatially averaging an output of said digital filter with corresponding outputs for nearby locations in the target region.

17. The apparatus of claim 16, wherein said contrast-preserving temporal filter comprises a time-varying, first order, infinite impulse response filter designed to have a fast attack time during a systolic cycle period and a slow decay time during a diastolic cycle period.

18. The apparatus of claim 13, the sequence of frames of pulse-echo ultrasound data comprising digital samples, the digital samples being taken at a sampling frequency, wherein said demodulator comprises:

a quadrature mixing device, said quadrature mixing device having a mixing frequency of one quarter of said sampling frequency, said quadrature mixing device comprising a half-band filter having a cutoff frequency of one-quarter of said sampling frequency, said quadrature mixing device for performing mirror-cancellation on said digital samples to produce intermediate signals; and a complex mixer for rotating said intermediate signals to the baseband frequency to produce said in-phase component and said quadrature component.

19. The apparatus of claim 18, said sequence of frames of pulse-echo ultrasound data being associated with reflections from an ultrasound transducer generating acoustic bursts at a carrier frequency, wherein said complex mixer has a mixing frequency equal to one quarter of said sampling frequency minus said carrier frequency.

20. The apparatus of claim 19, said sequence of frames of pulse-echo ultrasound data being associated with reflections from an ultrasound transducer generating acoustic bursts at a carrier frequency, wherein said complex mixer has a mixing frequency equal to one quarter of said sampling frequency minus said a first frequency function, said first frequency function being a swept frequency function between a minimum frequency value and a maximum frequency value.

21. An apparatus for processing a sequence of B-mode echo frames received from a target region, comprising:

a demodulator for demodulating the B-mode echo frames into component baseband signals for each location in the target region;

a phase detector for deriving phase information from said component baseband signals for each location in the target region for each frame; and a flow detector for deriving a flow image value at each location in the target region by detecting changes in said phase information across multiple B-mode frames for that location;

whereby a flow image may be derived from said flow image values, said flow image having a frame rate and spatial resolution similar to that of standard B-mode images that may be derived from the sequence of B-mode echo frames.

22. The apparatus of claim 21, wherein each of said flow image values is proportional to a fluid flow velocity at its respective location, whereby said flow image forms a non-aliased color Doppler ultrasound display for those locations having a flow velocity less than a B-mode Nyquist velocity or an aliasing display above the Nyquist velocity.

23. The apparatus of claim 22, wherein said B-mode Nyquist velocity is proportional to (i) a B-mode frame rate times the speed of sound in the target region, divided by (ii) a B-mode carrier frequency times the cosine of a Doppler angle for that location.

24. The apparatus of claim 21, the sequence of B-mode echo frames comprising digital samples taken at a sampling frequency, the component baseband signals comprising an in-phase component and a quadrature component, wherein said demodulator comprises:

a quadrature mixing device, said quadrature mixing device having a mixing frequency of one quarter of said sampling frequency, said quadrature mixing device comprising a half-band filter having a cutoff frequency of one-quarter of said sampling frequency, said quadrature mixing device for performing mirror-cancellation on said digital samples to produce intermediate signals; and a complex mixer for rotating said intermediate signals to the baseband frequency to produce said in-phase component and said quadrature phase component.

25. The apparatus of claim 24, said flow detector being adapted and configured to perform the steps of: computing a temporal difference sequence at each location corresponding to changes in said phase information at that location across multiple B-mode echo frames; computing a phase shift metric from said temporal difference sequence; comparing said phase shift metric with a first threshold value; and setting said flow image value to a null value if said phase shift metric is less than said threshold value for indicating the absence of flow at that location.

26. The apparatus of claim 25, further. comprising an input device for allowing a user to dynamically adjust said first threshold value for optimizing said flow image.

27. The apparatus of claim 26, said flow detector being further adapted and configured to set said flow image value to non-null value if said phase shift metric is greater than said first threshold value for indicating the presence of flow at that location.

28. The apparatus of claim 27, said flow detector being further adapted and configured to setting said flow image value to a color-coded identifier corresponding to a magnitude of said phase shift metric if said phase shift metric is greater than said first threshold value for indicating both the presence of fluid flow and the phase shift metric magnitude corresponding thereto.

29. The apparatus of claim 28, said flow detector being adapted and configured to compute said phase shift metric from said temporal difference sequence by performing the steps of: computing an average difference sequence from said temporal difference sequence by averaging each element therein with at least one neighboring element; replacing each element in said average difference sequence with its absolute value; filtering said average difference sequence with a contrast-preserving temporal filter; and setting said phase shift metric equal to an output of said contrast-preserving temporal filter.

30. The apparatus of claim 29, wherein said contrast-preserving temporal filter comprises a time-varying, first order, infinite impulse response filter designed to have a fast attack time during a systolic cycle period and a slow decay time during a diastolic cycle period.

31. The apparatus of claim 25, further comprising:

an amplitude detector for deriving a B-mode image value from said component baseband signals for each location in the target region for each frame; and a selective flow image suppressor coupled to receive said flow image value and said B-mode image value and to selectively suppress said flow image value based upon a comparison of said B-mode image value with a predetermined upper threshold and a predetermined lower threshold, wherein said flow image value is reset to null if said B-mode image value is greater than said upper threshold value, and wherein flow image value is reset to null if said B-mode image value is less than said lower threshold value.

* * * * *